United States Patent [19]

Heslinga et al.

[11] 4,332,917
[45] Jun. 1, 1982

[54] METHOD OF PREPARING A POLYMER MIXTURE, FORMED PRODUCTS OBTAINED THEREFROM AND POLYMER ALLOY

[75] Inventors: Adolf Heslinga, HD Pijnacker; Pieter J. Greidanus, MK Leiden, both of Netherlands

[73] Assignee: Nederlandse Centrale Organisatie voor Toegepast-Natuurwetenschappelijk Onderzoek, The Hague, Netherlands

[21] Appl. No.: 105,750

[22] Filed: Dec. 20, 1979

[30] Foreign Application Priority Data

Dec. 22, 1978 [NL] Netherlands .......................... 7812529
Dec. 5, 1979 [NL] Netherlands .......................... 7908799

[51] Int. Cl.³ .................... C08L 33/02; C08L 1/12; A61K 47/00; C08F 6/10
[52] U.S. Cl. ..................................... 521/134; 424/78; 525/192; 525/193; 525/194; 525/197; 525/198; 525/207; 528/501; 524/37; 524/40; 524/41; 524/549
[58] Field of Search ................ 260/17 R; 521/134

[56] References Cited

U.S. PATENT DOCUMENTS

| | | | |
|---|---|---|---|
| 2,798,053 | 7/1957 | Brown | 521/38 |
| 3,939,123 | 2/1976 | Matthews et al. | 528/60 |
| 3,983,095 | 9/1976 | Bashaw et al. | 526/15 |
| 4,073,754 | 2/1978 | Cabasso et al. | 260/17 R |
| 4,097,429 | 6/1978 | Elghani et al. | 260/17 R |
| 4,160,754 | 7/1979 | Schäpel et al. | 260/29.4 R |
| 4,192,727 | 3/1980 | Ward | 204/159.12 |
| 4,263,183 | 4/1981 | Light et al. | 260/17 R |

FOREIGN PATENT DOCUMENTS

| | | |
|---|---|---|
| 7401887 | 8/1974 | Netherlands . |
| 7507186 | 6/1975 | Netherlands . |
| 7710816 | 10/1977 | Netherlands . |
| 7803089 | 3/1978 | Netherlands . |
| 1200106 | 7/1970 | United Kingdom . |

OTHER PUBLICATIONS

Encyclopedia of Polymer Science & Technology, vol. 15, pp. 273-291, Wiley, N.Y., 1971.

*Primary Examiner*—H. S. Cockeram
*Attorney, Agent, or Firm*—Bert J. Lewen

[57] ABSTRACT

Method for preparing a polymer alloy which is stable and homogeneous up to high temperatures, from component (a) one or more polymers of high molecular weight, having anhydride groups and component (b) one or more polymers of high molecular weight, having groups which have the ability to interact with hydrogen atoms to form hydrogen bonds, wherein first a solution of component (a) is prepared in an organic solvent, to which solution then component (b) is added, whereas component (a) in dissolved state is protolyzed in whole or in part, prior to or after the addition of component (b) under the action of protolyzing agents, whereupon the solvent is removed; together with the formed products obtained from such a polymer alloy, such as granules, fibres, foils, foam, etc.

16 Claims, 5 Drawing Figures

REACTION EQUATIONS

METHOD OF PREPARING A POLYMER MIXTURE, FORMED PRODUCTS OBTAINED THEREFROM AND POLYMER ALLOY

The invention relates to a method for preparing a polymer mixture, to formed products obtained therefrom, such as granules, fibres, foils, foams, etc., and polymer alloy.

It has already been proposed to prepare moisture-absorbent and/or extensively swelling polymers of unsaturated carboxyl compounds, such as maleic anhydride, by polymerizing the carboxyl monomer with a cross-linking agent, such as a polyethylene-unsaturated compound, according to the method specified in U.S. Pat. No. 2,798,053. Such polymers were used as synthetic gums in the preparation of sticky or gel-like aqueous mixtures.

It is known from British Pat. No. 1,200,106 that certain weakly cross-linked polymers with a large number of hydrophilic units can be advantageously used for absorbing and binding liquids. As described in U.S. Pat. No. 4,192,727, such polymers, e.g. slightly crosslinked, partly hydrolized poly acrylamides, have been recommended as components of the filling material for disposable diapers, of fillings for beds and of other similar sanitary products because of their ability to retain appreciably more aqueous liquid under pressure than is the case with the use of an equal amount of fluffy cellulose or similar material. In some applications of such extensively water-swellable polymers, however, difficulties have been encountered in containing the polymer after it has been saturated with the aqueous liquid. It would be desirable to have an extensively water-swellable, water-insoluble polymer in fibrous form, such as has been described in more detail in U.S. Pat. No. 3,983,095.

Further, it is in general desirable to have polymers with an adjustable capacity of moisture absorption.

U.S. Pat. Nos. 4,160,754 and 3,939,123, have furthermore described water-swellable and/or water-absorbent materials obtained by other cross-linking reactions, such as between polyisocyanates and polyols. Moreover, many moisture-sensitive or swellable plastics have been developed on the basis of water-soluble polymers, such as polyacrylic acid, polyacrylamide and derivatives thereof, combined or not combined with naturally occurring hydrophilic polymers, such as starch, cellulose and derivatives.

These materials are known as synthetic hydrogels. In many cases they are manufactured in the form of powders, fibres, granulates, foils, etc. They are used, among other things, for medical and sanitary purposes. In this context, cf. *Encyclopedia of Polymer Science and Technology*, 15, 273–291.

These as well as the many other water-soluble or water-degradable packaging materials which are now available entail major drawbacks. Specifically, the processability at high temperatures (such as 120° to 200° C.), which are customary in the processing of thermoplastics, often raises great difficulties. This is particularly so when polymers having side groups are to be raised to elevated temperatures. Crosslinking reactions often cause the initially thermoplastic characteristics to be lost, so that continuous processing at high temperatures also becomes very hard or impossible to implement.

On the other hand, many hydrophilic polymers, such as polyvinyl alcohol, cellulose, starch and derivatives, mostly have very high melting or softening ranges, or none at all. In such cases, too, the conventional thermoplastic processing techniques cannot be implemented or are very hard to operate.

In addition, cross-linking reactions usually take place as well, or dehydration sets in, causing the original structures to be irreversibly changed.

Accordingly, there is a need for synthetic polymers having hydrophilic properties (cf. starch, proteins, cellulose), which can be prepared and processed according to the available technology for thermoplastics (extrusion, injection moulding, foil extrusion, calendering, etc.) without untimely irreversible changes or reaction taking place during these processes.

The invention aims at providing a method of preparing hydrophilic synthetic polymers, with the use of which the drawbacks of the prior art preparation methods are effectively obviated.

To this end, the method according to the invention is characterized in that a polymer alloy is prepared which is stable and homogeneous up to high temperatures, starting mainly from component (a) one or more polymers of high molecular weight having anhydride groups and component (b) one or more polymers of high molecular weight with groups which have the ability to interact with hydrogen atoms to form hydrogen bonds wherein first a solution of component (a) is prepared in an organic solvent, to which solution then (b) is added; component (a) in dissolved state is protolyzed in whole or in part, prior to or after the addition of (b), under the action of protolyzing agents, whereupon the solvent is removed, whereas (a) and (b) each has a molecular weight of at least $10^4$.

In general component (a) has highly polar characteristics, but is nevertheless insoluble in water. Under the influence of water, however, depending on pH and temperature conditions, it passes into a water-soluble polymer because of the formation of free carboxyl groups or carboxylate ions. The solubility in water is a function of pH.

For the purposes at hand, (a) and (b) are to have a molecular weight amounting to at least $10^4$.

A very important aspect of the invention in preparing this homogeneous polymer alloy is that, generally speaking, substances of high molecular weight which are constituted by different chemical structures are not or hardly homogeneously miscible in all proportions (cf. among others, *Encyclopedia of Polymer Science and Technology*, 20, 694–697). The preparation of homogeneous polymer alloys is generally impossible or very difficult.

It has now surprisingly been found that the copolymer of styrene and maleic anhydride (SMA) (a) and polyvinyl acetate (PVAc) or cellulose triacetate (CTA) or cellulose aceto butyrate (CAB) or polyethyl acrylate (PEtA) or polymethyl methacrylate (PMMA) (b), are miscible in all proportions below certain temperatures. This is caused by slight interaction between the polymer species (a) and (b). At a specific temperature, however, segregation or phase separation will take place. This temperature is called the critical temperature, Tc. This Tc is a function of the molecular weights of the components and the mutual weight ratio.

It has furthermore been found that miscibility at high temperatures (100°–200° C.) can be adjusted by increasing the physical interaction (association) of the polymer components.

This increased interaction can be brought about by partial hydrolysis (generally protolysis) of component (a), before or after the addition of (b). The protolysis introduces carboxyl groups along component (a), which furnish hydrogen bonds for the association between (a) and (b).

It is of major importance to conduct the preparation of protolyzing of (a), after (a) has been dissolved in an organic solvent, in order to get a homogeneous reaction.

Of the polymers which enter as component (b) into the polymer alloy according to the invention polymers having ester side groups are preferred, such as vinyl esters, cellulose esters, acrylic esters or methacrylic esters. An instructive example of polymer alloys according to the invention is the alloy consisting of a copolymer of styrene and maleic anyhydride (a) and polyvinyl acetate (b). With this alloy we show the principal effects of the invention, i.e. "solvent alloying".

In order to further illustrate the invention, the following figures are attached:

Figure 4:
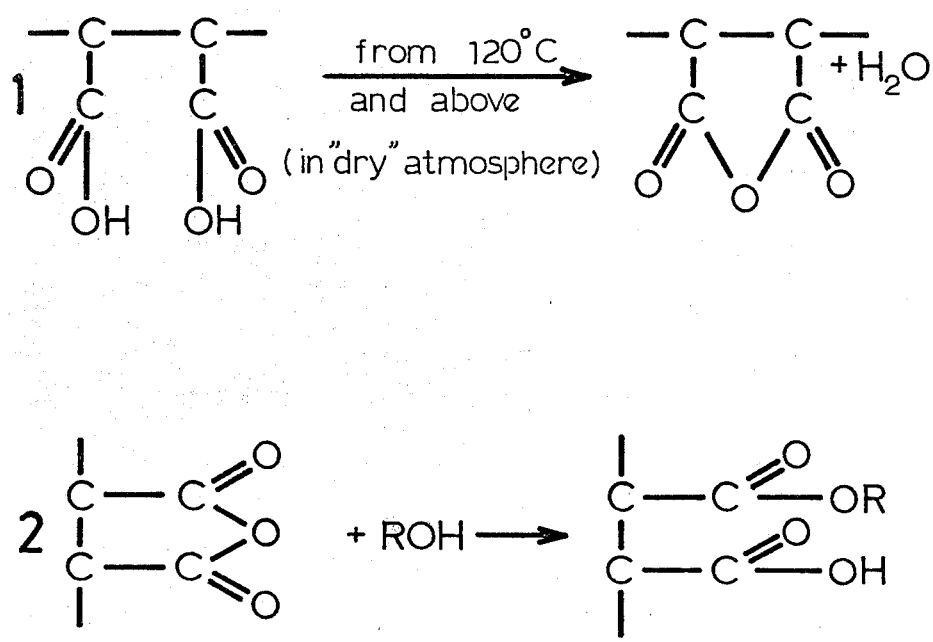

FIG. 4, entitled "Reaction Equations", shows, in Equation 1, the dehydration reaction of the hydrated or hydrolyzed copolymers in a dry atmosphere and Equation 2 shows the formation of a semi-ester during the protolysis reaction.

Figure 1:
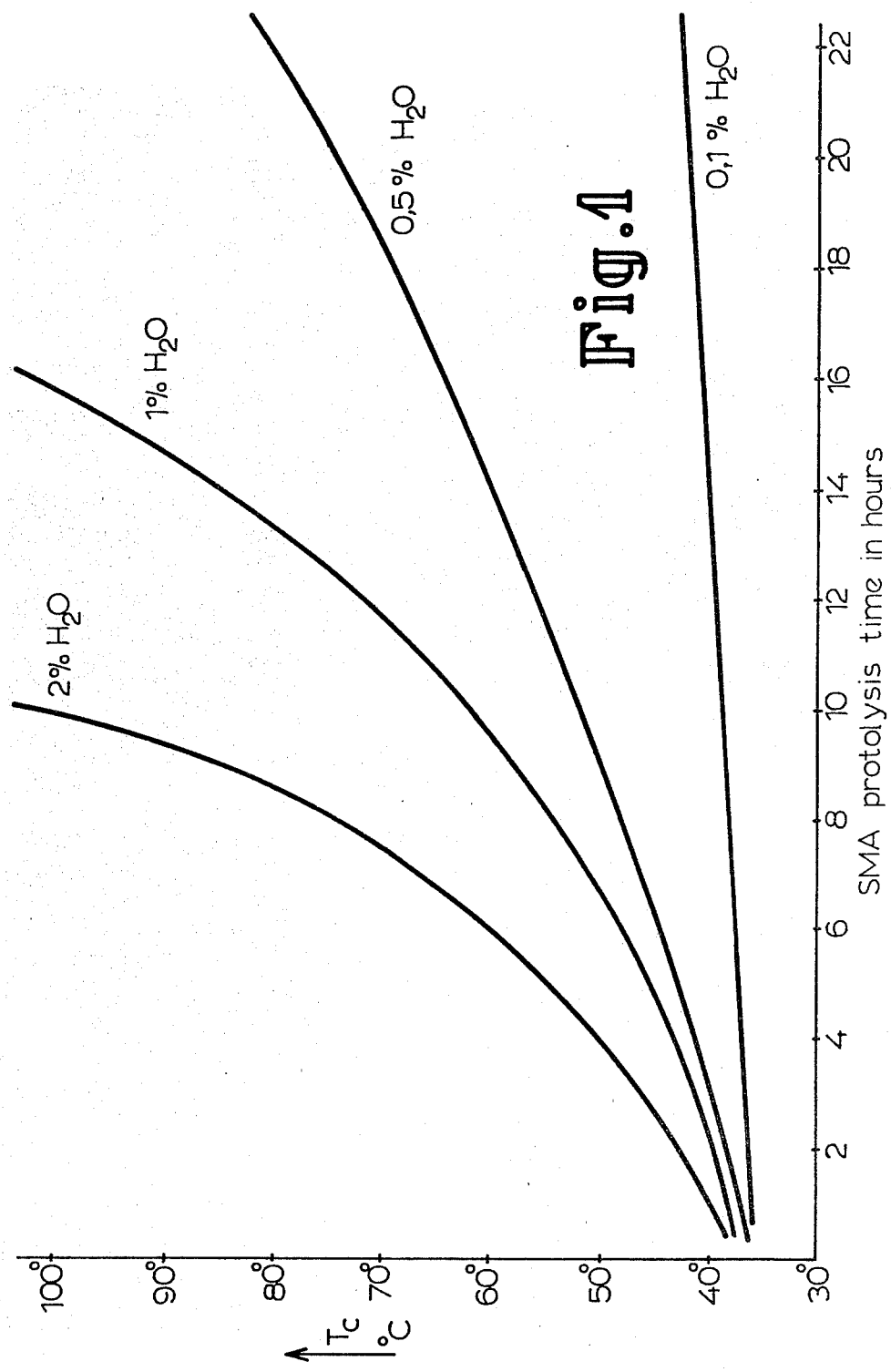
FIG. 1 shows the relationship of protolysis time and critical temperature, Tc, for solutions of polymer alloys containing various amounts of water.

The manner of evaporation of the solvent, or drying, forms an important part of the present invention. Specifically, it should be carried out in such way that the aformentioned increased interaction is maintained. The successive manners of preparation are as follows:

A mixture of both polymers (SMA and PVAc) is prepared by starting from a solution in, for example, butanone (methyl-ethyl ketone). Prior to this, the copolymer is prepared separately by way of a so-called solution polymerization of an alkene, such as styrene and maleic anyhydride, or dissolved as a ready polymer. Following the completed polymerization up to a given molecular weight, partial protolysis is effected by adding f.c. some water or alcohol to the polymer solution. Heating and catalysts will accelerate the protolysis. Consequently, continuous heating of the solution of SMA increases the Tc. The increase of Tc can be expressed in a functional form versus time, concentration and temperature (FIG. 1).

After the protolysis the poly vinylacetate is added to this solution, either in solid form or likewise as a solution in butanone, whereupon mixing takes place.

Although the concentration of the solution is not essential, a solution of about 20 percent polymer content is generally prepared for practical reasons. The dissolving technique used is of major importance for obtaining an optimum degree of homogenization. Association of the two kinds of polymers (a) and (b) in the solvent allows the alloying effect to be attained in a short time to a maximum and effective extent. The degree of association (a) . . . (b) has been increased by partial hydrolysis (protolysis) of the copolymer as described.

The solid homogeneous polymer alloy can then be obtained by a drying process in which the solvent is evaporated (distilled) in a closed system at temperatures ranging from 100° to 200° C. (generally 130° to 160° C.).

The distillation or drying process can be accelerated by working under reduced pressure (for example 10 to 500 mm/Hg). The drying process is to be implemented in a closed system for the following reasons:

(1) Recovery of the solvent.

(2) The drying process should take place in an atmosphere having a certain degree of humidity. A fully "dry" environment should be avoided. The reason for this is that copolymers having anhydride groups which are hydrated or hydrolyzed in whole or in part are known to be reconverted by dehydration into the cyclic anhydride configuration (the reaction reverses). (In this connection, cf. reaction equation 1 of FIG. 4.) As a result, the association is reduced, and phase segregation can again take place. The drying process should therefore take place in highly specific conditions. It has surprisingly been found that in certain conditions during drying it is not a decrease that can be obtained but, rather, an increase.

(3) The drying process can also be combined, as it were, with the hydration or hydrolysis reaction.

An increase in water content takes place during the drying process, since butanone boils at 80° C. and water at 100° C. A certain fractionating effect takes place.

In combination with the rapid rise of temperature during the drying process, a rapid conversion presently sets in from anhydride groups to COOH groups in the closed system.

The relation between the temperature and the state of the resin takes the following course in the drying apparatus:

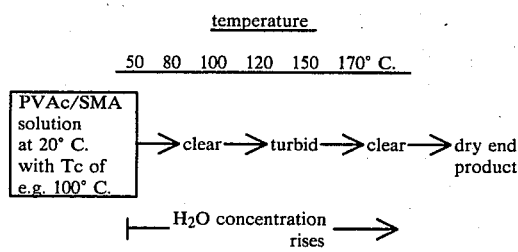

The Tc rises as a result of fast protolysis by $H_2O$ beyond 100° C.

(4) Further to point (3) it is evident that all kinds of added substances with reactive functions, such as alcohols, can be chemically bonded during the drying process by way of residual anhydride groups. In this connection, cf. the reaction equation 2 of FIG. 4, where a rapid protolysis reaction takes place in the apparatus at an elevated temperature during the drying process, while yielding a semi-ester.

(5) It naturally is also possible to add the widest variety of substances before the drying process: plasticizers, modifiers, adjuvants, fillers, pigments and dyes, lubricants, biologically active substances, etc.

The polymer alloys at issue have the following properties: thermoplastic; clear; density about 1.2 to 1.3 g/cm$^3$; softening and processing temperatures from 100° to 200° C.; excellent resistance to aliphatic hydrocarbons, oils and fats; soluble in lower alcohols and ketones; capable of swelling in aromatic hydrocarbons.

The mechanical properties of the polymer alloys according to the invention are a function of the molecular weights of the components and of the mutual ratio a/b of the two polymers. Example: High PVAc contents lower the modulus of elasticity or raise the elongation at break (see Table A). The modulus (or the rigidity) can be further lowered by adding plasticizers and/or other modifiers (see Table B).

TABLE A

TENSILE TESTING OF FOIL SAMPLES (POLYMER ALLOY OF SMA AND PVAc); STRIPS (1.5 cm WIDE) LENGTHWISE FROM SAMPLES. FIXED LENGTH, 10 cm; DRAWING RATE, 3 cm/min.; THICKNESS, ca. 0.1 mm.

| Foil composition | Yield stress, kgf/cm$^2$ | | Ultimate stress kgf/cm$^2$ | | Elastic modulus, kgf/cm$^2$ | | Elongation at break, percent | |
|---|---|---|---|---|---|---|---|---|
| a/b-SMA/PVAc | Aver. | S.A.* | Aver. | S.A.* | Aver. | S.A.* | Aver. | S.A.* |
| Copolymer No. 10 | | | | | | | | |
| 10/90 | 138 | 9 | 113 | 8 | 7,000 | 2,000 | 250 | 40 |
| 20/80 | 211 | 8 | 139 | 5 | 11,000 | 1,200 | 90 | 40 |
| 30/70 | 425 | 15 | 410 | 80 | 17,000 | 2,500 | 6 | 3.0 |
| 40/60 | — | — | 487 | 4 | 15,000 | 3,000 | 2.3 | 0.2 |
| Copolymer No. 9 | | | | | | | | |
| 10/90 | 97,0 | 3,0 | 101 | 3 | 6,500 | 2,000 | 294 | 8 |
| 20/80 | 185 | 9 | 134.5 | 1.5 | 10,500 | 1,300 | 220 | 25 |
| 30/70 | 343 | 9 | 201 | 10 | 16,500 | 2,000 | 35 | 9 |
| 40/60 | — | — | 470 | 40 | 20,800 | 1,200 | 2.6 | 0.3 |

*S.A. = standard deviation

TABLE B

EFFECT OF PLASTICIZERS; POLYMER RATIO, ca. 1:1 (50/50); PLASTICIZER CONTENT, ca. 30 percent.

| Plasticizer code | Ultimate stress | Yield stress | Elastic modulus | Elongation at break |
|---|---|---|---|---|
| PPA | 135 | 71 | 3000 | 220% |
| SPA | 133 | 152 | 5000 | 59% |
| Polyethylene comparison material | 150 | 120 | 2400 | 400% |

PPA = pentaerythritol diacetate-dipropionate
SPA = sorbitoltriacetate-tripropionate This new type of polymer alloys according to the invention can be processed with the use of the customary techniques for extrusion from melts and of the apparatus or techniques for casting from organic solvents. Foils can be fabricated according to known foil blowing techniques. Extrudates and granulates are obtained by standard extrusion techniques.

Fibres can be manufactured according to the usual techniques; monofilaments, for example, from the melt by dry spinning techniques or by wet spinning techniques on the basis of direct coagulation from organic solvents in water or aqueous solutions.

All new compositions according to the invention possess the advantage of being extrudable from the melt, either as such or in combination with suitable plasticizers. Suitable plasticizers are here defined as those substances which are adequately compatible with the polymer mixtures and do not give rise to undesired exudation, phase segregation, reactions, etc.

The polymeric material is characterized by the simultaneous presence of hydrophobic and hydrophilic groups. This manifests itself in a typical characteristic of these types of polymer alloys, i.e. their swellability, particularly in water (see FIG. 3). Swellability in polymer mixtures points to mixing of the polymer components at a molecular scale (=alloying) and also to strong interaction between the different polymer species.

The polymer alloy furthermore has the properties of polyanhydride resins; the presence of the anhydride group causes the alloy to be reactive even in solid form, so that secondary chemical reactions are possible.

Reactions are possible, for instance, with water, alcohols, ammonia, amines, epoxy compounds, and others. (In this connection, cf. the reaction equation 2 of FIG. 4) Secondary reactions have been used in order to improve the processability of the alloy during processing (cf. extrusion).

A few percents of fatty alcohol such as stearyl alcohol were added to the polymer solution before drying. The formed stearyl esters act during processing as internal, non-exuding lubricants. Clearly, very many modifications, both with regard to chemical and to physical properties, have become possible in this manner (cf. secondary reactions). The hydrophilic as well as the hydrophobic characteristics can thus be increased and decreased.

This applies very specifically to conversion with water. The polymer alloys are stable in dry conditions. This is generally also true when materials are stored in normal atmospheric conditions with respect to temperature and relative humidity (50 to 60 percent).

Upon prolonged exposure to air of high humidity or in direct contact with water, a gradual conversion takes place from the anhydride group to the free dicarboxylic acid configuration. The polarity (hydrophilic character) thus increases while the modulus (brittleness), measured in dry conditions, rises simultaneously. As a result of the reaction of the polyanhydride to polyacid or polyelectrolyte, the material assumes the properties of a stable hydrogel. The degree of swelling in water is a function of the degree of ionization of the composition of the polymer alloy (polymer ratio) and of the pH of the aqueous medium. Maximum swelling takes place at, for example, pH=6-8, and minimum swelling at pH=2-3 (in buffered solution). This phenomenon is reversible and is comparable with the familiar behaviour in water of proteins, such as gelatin, keratin, and the like.

The hydrogel accordingly possesses the characteristic properties of a polyelectrolyte and can also function for example, in hydrogel form as an ion exchanger, such as in binding multivalent metal ions like Ca, Cu, Zn and Cd. The hydrogels and xerogels fabricated by hydrolysis from the polymer alloy are stable because of the extensive interaction of component (b) with the hydrolyzed or ionized component (a).

Very rapid conversion of the polyanhydridepolymer alloy into a hydrogel polyelectrolyte can be produced by strong bases like NaOH and KOH, and especially by ammonia, ammonia-in-water solutions and organic amines. Cross-linking takes place in reactions with bi- or polyfunctional compounds, such als glycols, di- and polyamines, etc. The degree of swelling of the hydrogels can thus be varied by modification as a result of reactions with both mono- and polyfunctional reactive compounds.

The polymer alloys according to the invention can serve for manufacturing synthetic products having a variety of properties.

The material can be in the form of granules, fibres, foils, powders and other forms known in the processing technology of polymeric materials. Of particular importance is the conversion by water into substances having hydrogel properties (or polyelectrolyte properties).

Especially important is the use of fibrous or powdery material in the form of a polyelectrolyte or salt for moisture absorption. Also possible is the use of hydrogels formed in secondary reactions, applied as ion exchangers in conventional methods.

As has been set forth hereinabove, the polymer compositions are caused to swell in the presence of water, after having been reacted with ammonia or organic and inorganic bases.

As a result, the polymer alloys are particularly suitable for manufacturing polymer compositions for regularly releasing active constituents, specifically under the action of water. Both the speed and the degree of swelling affect the delivery rate of the active constituents, thus allowing controlled delivery. The delivery rate naturally is also a function of form and size of the polymer mixtures (granules, powders, foils, fibres, etc.). Active substances may comprise such products as insecticides, fungicides, herbicides; generally: biocides, feromones, etc., repellents for the control of pests, plant diseases or the attack on plants by insects and/or other harmful organisms. Another possibility consists in the controlled delivery of pharmacologically active substances.

If the polymer alloys are prepared in fibrous form, they can be converted after the secondary reaction by treatment with ammonia, amines strong bases, etc., into fibres having a high swelling capacity or moisture absorbency in water.

The completed, water-insoluble and water-swellable fibres are suitable for many purposes. These fibres can primarily be used in the manufacture of absorbent layers for sanitary products.

The above application can likewise be implemented in the form of foils, films of thin sheets or strips, etc. The swellability or absorbency is primarily a function of the mutual ratio of the two polymers in the polymer alloy. Elevated concentrations of component (a) increase the swellability after secondary hydrolysis and/or ionization to hydrogel structures.

During the preparation of the polymer alloy at hand, it is also possible to add fillers, such as carbon black, chalk, fibres, etc.

The addition of a foaming agent during preparation can likewise be advantageous for obtaining porous structures.

The invention also comprises new, up to high temperatures stable and homogeneous polymer alloys prepared from component (a) one or more polymers of high molecular weight, and component (b) one or more polymers of high molecular weight which are able to interact with hydrogen, in which alloy the components (a) and (b) by protolyzing component (a) in whole or in part, are linked by hydrogen bonds.

The new polymer alloys according to the invention comprise as component (a) one or more copolymers of high molecular weight of an alkene unsaturated monomer and maleic anhydride, and as component (b) polymers containing ester groups.

The component (a) in the polymer alloy according to the invention usually is styrene-maleic anhydride copolymer while the component (b) usually consists of polyvinyl acetate, a cellulose ester, polyacrylate or polymethacrylate.

Furthermore the polymer alloy according to the invention may comprise an additional component and/or material. Examples of additional components that can be used are an active material, such as insecticides, fungicides, herbicides, etc., or a reactive component for modification of the polymer alloy during its preparation, or a foaming agent. As additional material for the alloy a filler, such as carbon black, chalk, fibres, etc., can be added.

EXAMPLE I

Preparation of the copolymer SMA in methylethyl ketone as solvent (i.e. solution polymerization).

In a vessel having a capacity of about 50 l, the following substances were successively mixed:

30 l (25 kg) of methyl-ethyl ketone (butanone), 3120 g of styrene, 3000 g of maleic anhydride, 7.5 g of azobis-isobutyronitrile (catalyst).

The vessel was equipped with a heating jacket, a stirrer, a thermometer and a thermal safety device. The contents were heated while being stirred continuously, and maintained at a certain temperature for a certain time.

Example of a heating scheme:
Heating to 60° C., 1 h
Constant at 60° C., 2 h
Constant at 70° C., 1 h
Constant at 80° C., 3 h
Total polymerizing time, ca. 7 h
Viscosity, ca. 450 centipoises
Solid matter content, ca. 20 percent
Critical segregation temperature Tc=41° C. (measured with PVAc solution; see Example II and FIG. 1).

The degree of polymerization can be varied by changing the catalyst concentration and the reaction temperature.

Measurements of the intrinsic viscosity allow the approximate determination of the molecular weight (*J. of Applied Polymer Science* 20: 1619 [1976]).

Molecular weight, generally, m=$10^4$ to $10^5$ 10,000 to 100,000.

The solid polymer can be obtained by evaporation of the solvent or by precipitation in excess methanol.

EXAMPLE II

Partial hydrolysis of the copolymer of styrene and maleic anhydride of Example I in solution. Partial hydrolysis for raising the critical segregation temperature, Tc.

The critical segregation temperature, Tc, is a phase-transition temperature and was measured by mixing approximately equal parts of the copolymer solution of 20 percent in butanone and respectively a polyvinyl acetate solution, PVAc, (M70, Hoechst), a cellulose triacetate solution (Tenite I, Eastman Kodak), a cellulose-aceto-butyrate solution (Tenite II, Eastman Kodak) and a poly ethyl acrylate, PEtAcr, (synthesized in the laboratory), all of 20 percent in butanone. At Tc this mixture suddenly turned turbid as a result of segregation (cf. melting point, determination of boiling point).

Upon completion of the polymerization of styrene maleic anhydride as described in Example I, to samples of the polymer solution respectively 0.1, 0.5, 1 and 2% water by weight was added with vigorous stirring (water content of total solution thus amounts to about 0.1, 0.5, 1 and 2%). These water containing solutions were heated for about 20-30 hours at 75° C. During heating the critical segregation temperature, Tc, was determined for the mixtures of the samples and the polyvinyl acetate (PVAc) solution. The rate of protolysis and therefore the rise of Tc, is a function of the reaction temperature and of the water concentration. FIG. 1 shows the protolysis and therefore the rise of Tc for the PVAc/SMA mixture as a function of the water concentration and the protolysis time at 75° C. The temperature dependence of the rise of Tc was illustrated by the fact that for the PVAc/SMA mixture a Tc of 100° C. in butanone was yielded after 40 days storage of the SMA solution with 1% water at 20° C., while using a SMA solution with 2% water and heated at 75° C. already after 8 hours a Tc value of 100° C. had been yielded.

At different times, after heating at 75° C. and therefore at different protolysis times, samples of the copolymer solution, containing 1% water by weight, were mixed with respectively solutions of 20% cellulose triacetate, cellulose aceto butyrate and polyethyl acrylate, after which the Tc was determined.

Figure 2:
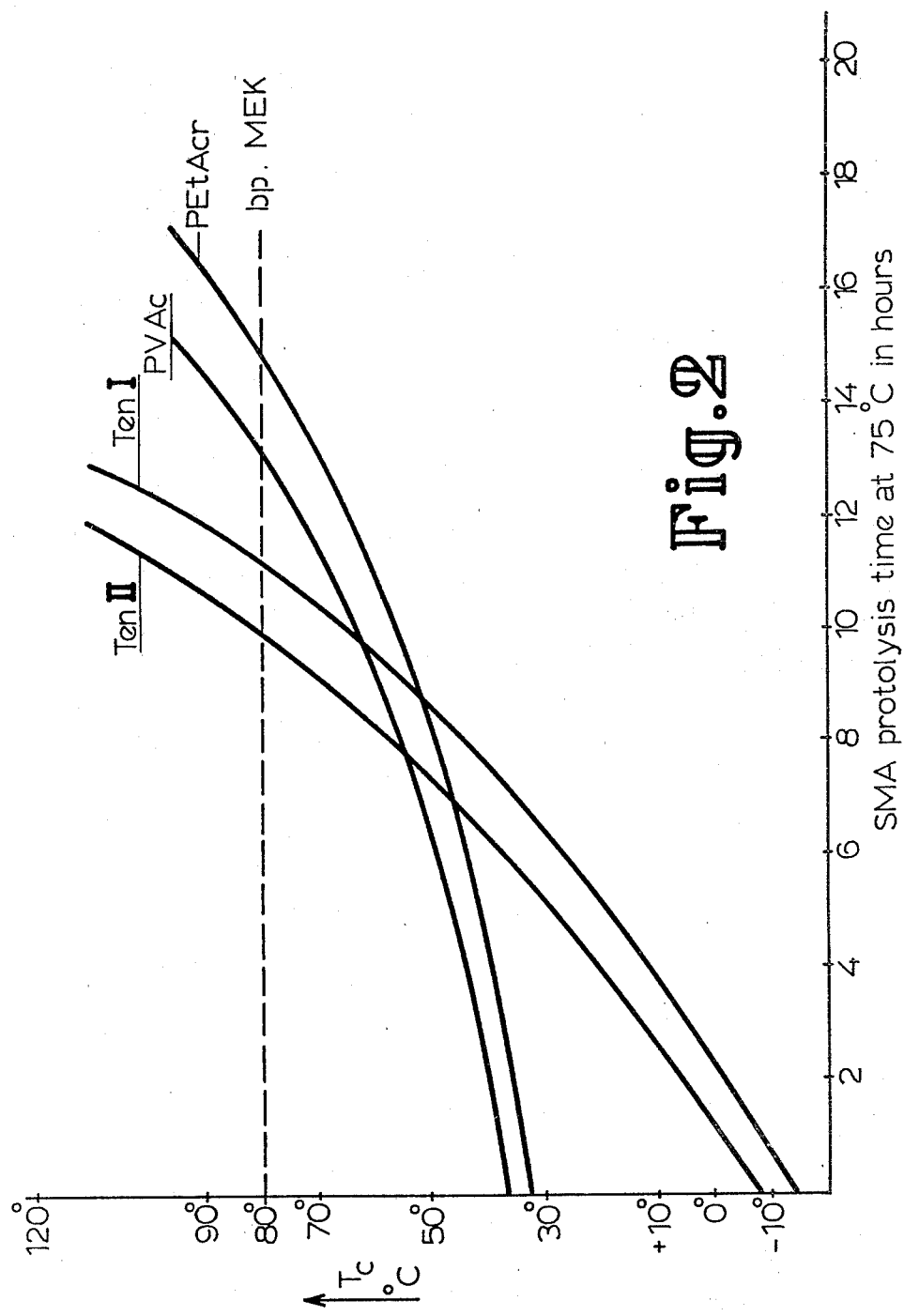
FIG. 2 shows the relationship of pyrolysis time and critical temperature for solutions of polymer alloys containing copolymers of styrene-maleic anhydride and, respectively, poly(vinyl acetate) cellulose triacetate, cellulose acetobutyrate and poly(ethyl acrylate).

In FIG. 2 the rise of Tc as a function of protolysis time at 75° C. is shown. In these examples all Tc values were measured in solutions containing equal parts by weight of the polymer components which form the polymer alloy.

EXAMPLE III

Preparation of the polymer alloy (30:70 proportion)

10 kg of the 20 percent copolymer solution of Example I was protolyzed with 10 g water at ca. 75° to 80° C. for about 16 hours. The Tc rose up to about 100° to 110° C. The following substances are mixed with this protolyzed copolymer solution in a vessel (boiler) having a capacity of 50 l:

19.6 kg of methyl-ethyl ketone (MEK), 4.66 kg of polyvinyl acetate (Mowilith-70 commercial polymer, Hoechst). The PVAc (M70) is a suspension or bead polymerizate of Hoechst (Frankfort, Germany).

The (solid) polyvinyl acetate was dissolved with slow stirring until a clear solution had been formed.
Mixing temperature, ca. 15° to 20° C.;
Total solution of polymer alloy, 34.30 kg;
Solid matter content, 20 percent;
The SMA/PVAc mixing proportion is 30:70.

Naturally it is possible to carry out the mixing operation with certain polyvinyl-acetate solutions in MEK. Predissolved PVAc has the industrial advantage of rapid mixing with copolymer solutions.

Clearly, all desired polymer proportions can be rapidly obtained according to Example III.

The drying process:

Ca. 1000 kg of the polymer alloy of Example III were dried with the aid of an industrial dryer (Luwa Filmtruder). Before this, ca. 2 kg of stearyl alcohol (internal, non-exuding lubricant; $C_{18}H_{37}OH$) were stirred into this solution, in order to improve the processability of the solid alloy during processing.

Use may naturally be made of other similar dryers as well.

Prior to drying, a variety of substances can be added (if required) to the solution of polymer alloy: plasticizers, lubricants, stabilizers, modifiers, biologically active substances, dyes and pigments, fillers, etc. In Example IV, for instance, a fatty alcohol, i.e. stearyl alcohol (a lubricant) is added for improving the extruding properties of the dry polymer alloy.

EXAMPLE IV

Using the Luwa Filmtruder mentioned in Example III, the following drying tests were carried out:

| Test no. | Input, kg/h | Wall temp., °C. | Vacuum, mm of Hg | Yield of solid polymer alloy, kg/h | Appearance of polymer alloy |
|---|---|---|---|---|---|
| 1 | 75 | ca. 160 | 300 | 17 | turbid |
| 2 | 60 | ca. 160 | 400 | 14 | slightly turbid |
| 3 | 60 | ca. 180 | 400 | 15 | clear |
| 4 | 50 | ca. 180 | 500 | 12 | clear |
| 5 | 75 | ca. 180 | 200 | 18 | slightly turbid |

The solid matter content of the extrudate was about 98 percent. The original Tc was about 100° C.

An additional 1 percent of water was added to about 1000 kg of resin mixture of Example III, followed by 2 hours of stirring and heating at 70° to 80° C. As a result, the critical temperature, Tc, rises to above 140° C.

| Test No. | Input, kg/h | Wall temp., °C. | Vacuum, mm of Hg | Yield of solid polymer alloy kg/h | Appearance of polymer alloy |
|---|---|---|---|---|---|
| 6 [optimum] | 75 | ca. 160 | 300 | 16 | clear |
| 7 [too far] (Tc drops again) | 60 | ca. 190 | 200 | 15 | slightly turbid (drying carried too far) |

These examples clearly indicate that the clear homogeneous polymer alloy is only obtained in specific conditions.

EXAMPLE V

Starting from the solution of polymer alloy of Example III, drying tests have also been carried out with a closed roller dryer developed in our laboratory, the capacity of which was much smaller. Horizontal setup; two rollers with screw.

Input, ca. 7 kg/h (20 percent solution);
Wall temperature, 140° to 150° C.;
Vacuum, 300 to 400 mm of Hg;
Yield of polymer alloy, ca. 1.5 kg/h;
Appearance, slightly turbid.

The resultant polymer alloy which issued was a continuous extrudate having a solid matter content of about 98 to 99 percent. Residual moisture content, 0.5 to 1 percent. The extrudate can be granulated immediately upon cooling.

EXAMPLE VI

Test with solution of polymer alloy having a Tc of 80° C.

The dryer of Example V was charged with a polymer alloy solution prepared from copolymer solution according to Example I and M70 polyvinyl acetate in the proportion of 30:70. Drying was carried out in the conditions of test 5 in Example IV. The extrudate was now fully white, opaque and of heterogeneous composition (phase segregation of the polymer components). In contrast with clear extrudates, the extrudates of Example VI did not swell.

EXAMPLE VII

Test for demonstrating the increase of Tc during drying (homogeneous and clear end product)

2 percent of water were added to the copolymer solution of Example I (percentage of total substance), and the mixture was heated for 8 h at about 80° C. Tc was now about 90° C. This was followed by mixing with polyvinyl acetate and methyl-ethyl ketone; the proportion of polymers was 50:50.

Drying in the apparatus of Example V was carried out in de following conditions:
Input, 5 kg/h;
Temperature, 150° C.;
Vacuum, 400 mm;
Yield, 1 kg/h;
Appearance, colourless to light yellow, clear.

EXAMPLE VIII

Properties of the solid polymer alloy, prepared following Example III: density 1.2 to 1.3 g/cm$^3$.

Modulus of elasticity, depending on moisture content and mixture ratio 2,000 to 10,000 kgf/cm$^2$ (viscous to hard).

The granulate can be processed in standard outgassing extruders (double-screw), allowing the residual moisture content or solvent to be even further reduced. Thermal stability, 1 to 2 hours at 150° C.: slight increase in viscosity. 1 hour at 190° C.: some cross-linking; colour remains light yellow.

Moisture absorption at high humidity (100 percent relative humidity): about 5 percent for 30/70 polymer alloy.
In boiling water, after 1 hour, about 10 percent.
In normal conditions, the material is stable and permanently thermoplastic.

EXAMPLE IX

Preparation of blown foil (from polymer alloy plus plasticizer)

A solution of polymer alloy was prepared according to the method described and was composed of 50/50 SMA/PVAc polymer (1:1). Tc of the solution of polymer alloy exceeds 120° C. About 10 percent (related to dry matter content) of glycerin triacetate were added prior to desiccation. Following drying according to Example V, granulate was obtained with which blown foil was prepared according to a prior art technique.

Properties of foil:
Thickness of foil, 50 to 60μ; clear; modulus of elasticity, 2,000 to 3,000 kgf/cm$^2$; elongation, 200 to 250 percent; ultimate stress, about 100 kfg/cm$^2$.

The elasticity of the foils of polymer alloy is extensively a function of the moisture content of the material and/or the environment. Sensitivity to moisture can be controlled by the methods described on the basis of the nature of the plasticizers, modifiers, etc.

EXAMPLE X

Like Example IX. Proportion of polymers, 30:70. Plasticizer, 5 percent of dibutyl phthalate (on polymer basis).

EXAMPLE XI

Preparation of fibres (wet spinning method)

A solution of polymer alloy was prepared in butanone; solid matter content of the solution, approx. 40 percent; viscosity of the solution, 35,000 to 40,000 cps.

Using prior-art techniques and methods, the solution of polymer alloy was spun as a spinning liquid by wet-state injection into water as a coagulating bath of about 20° C.

The spinnerette had 15 apertures with a diameter of 0.05 mm. The solution ejected formed fibres in the form of monofilaments, which could be continuously wound.

The resultant strand had about 5 to 8 dtex (gr/10,000 m) after conditioning at 65 percent of R.H. (relative humidity), and the moisture content was 2 to 3 percent at 20° C. (dtex is a measure for filament thickness).

EXAMPLE XII

Melt-spinning test

From the granulate obtained according to example VII a fibrous polymer alloy was produced by existing melt-spinning techniques in suitable (prior-art) apparatus. The fibres can be ionized by posttreatment with ammonia or organic amines (obtaining then electrolytic properties), as a result of which a high water absorbency is obtained, depending on the proportion of the polymers.

The swelling capacity (ΔV) may range from 10–100 grammes water/grammes polymer alloy in deionized water.

In the polyelectrolyte form (being in the form of polyions), the fibers have properties of ion exchangers.

EXAMPLE XIII

To 20 percent of solution of polymer alloy in butanone according to Example III were added:

10 percent of Chlorfenvinphos (Birlane concentrate (Shell) insecticide, in relation to the solid polymer content, whereupon drying was carried out in the conditions described in Example IV, Test No. 3. The result consisted of 1.6 kg of dry extrudate, which was subsequently granulated. Part of the granules were ground to powder. The granules as well as the powder were used as a control agent, such as a soil insecticide. The delivery rate of the active substance can be regulated by partial or complete ionization of the polymer alloy, for example by water, ammonia, bases or other protolytic substances. Besides the delivery rate can also be regulated by adjusting the releasing surface area (cf. powder and granules).

As has been shown in Examples V and VI, as well as in Examples II, III, IV and VII, homogeneous blending (thus alloying) only is possible if the drying process has been carried out at temperatures below the critical segregation temperature, Tc of the polymer mixture. The homogeneity of the solid blend can be determined by conversion of the blend into a hydrogel by ionization in water with pH 7.0–7.5. In homogeneous blends it will not swell.

EXAMPLE XIV

Preparation of hydrogel (a) Polyalloy material prepared according to Example IV (No. 3, 4 or 6) can be converted by diluted (1 percent ammonia) or other bases into a solid hydrogel. Example: About 4 grammes of extrudate (platelet, ca. 4×2×0.5 cm) were immersed for about 24 h in 1 percent ammonia solution. Preliminary swelling for ca. 24 h. Swelling was then continued in neutral water. The water was replenished until maximum swelling had been attained (final pH=7.0 to 7.5).

Stable hydrogel, maximum swelling in neutral water amounted to about 25 to 30 times the original dry weight; water content of the hydrogel was about 96 to 97 percent. (30:70 polymer alloy).

Figure 3:
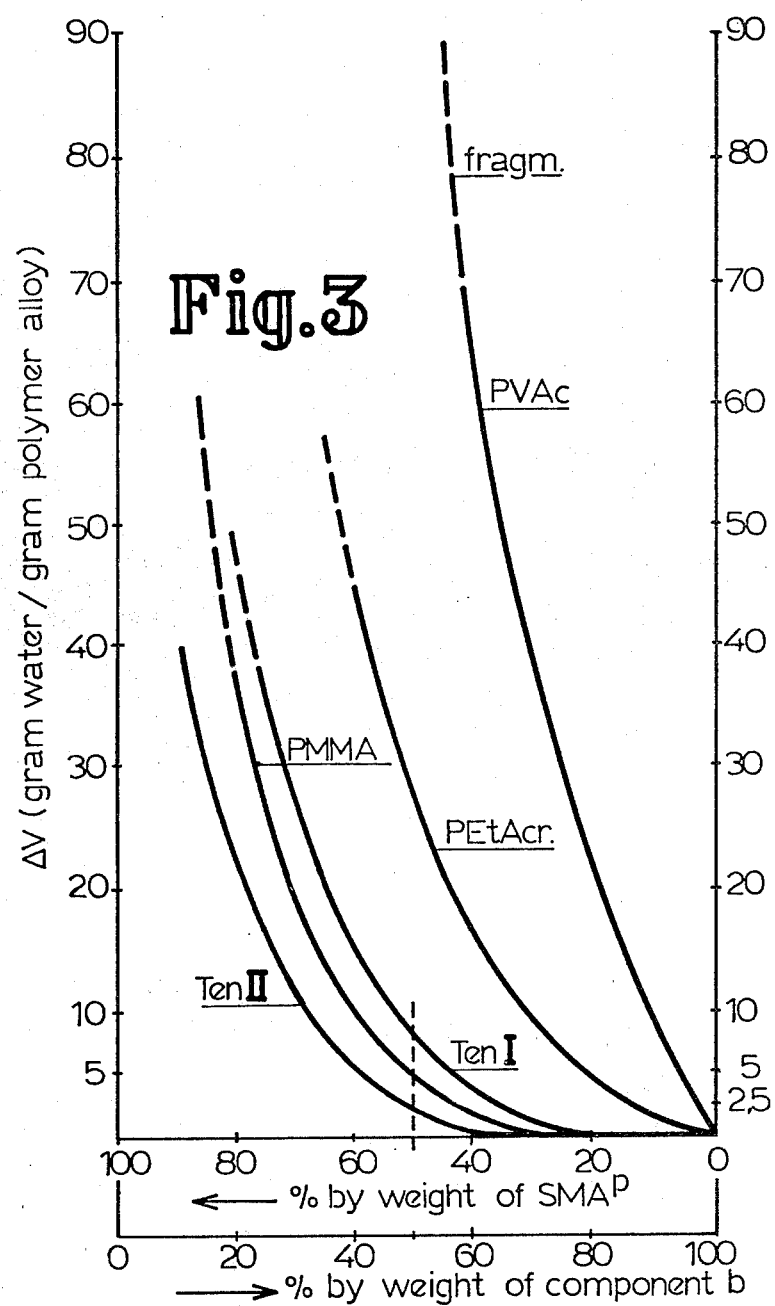
FIG. 3 shows the degree of swelling in water of hydrogels in relation to the ratio of the components (a) and (b).

(b) Poly alloy material was prepared as follows:

Solutions in butanone of polyvinyl acetate, PVAc, (M70, Hoechst), cellulose triacetate (Tenite I, Eastman Kodak), cellulose aceto-butyrate (Tenite II, Eastman Kodak), polyethyl acrylate, PEtAcr (synthesized in the laboratorium) and polymethyl methacrylate, PMMA, (Plexiglas, Röhm/Haas and Lucite, Dupont), component (b) (total amount ca. 20 percent), were mixed with SMA copolymer (a) solutions in butanone according to Example I, being respectively partly protolyzed to Tc values beyond 100° C. In FIG. 3 this protolyzed compound is indicated by $SMA^p$ (p=protolyzed). The solid polymer alloys were prepared by drying the respectively polymer mixture solutions at ca. 70° to 80° C. All solid samples were clear; no segregation had occurred. From these solid polymer alloy samples (films ca. 0.5 mm thick) hydrogels were prepared by the technique described in Example XIV (a). The equilibrium take-up of water or degree of swelling ($\Delta V$) in water of pH ca. 7.0–7.5 was measured as function of component ratio (a/b). The results are given in FIG. 3.

The volume increase ($\Delta V$) is as well a function of the a/b ratio as well of the whole molecular structure c.q. physical-chemical properties of component (b). It is clearly demonstrated that the hydrophility c.q. moisture absorbing capability of the various polymer alloys can be adjusted (regulated) by mixing more or less component (a) in the polymer alloy.

We claim:

1. A method for preparing a polymer alloy which is stable and homogeneous up to high temperatures, containing a component (a) which is one or more polymers of high molecular weight having anhydride groups and a component (b) which is a cellulose ester, comprising forming a solution of component (a) in an organic solvent; adding to such solution component (b), said component (a) in dissolved state being protolyzed in whole or in part prior to or after the addition of component (b) by a protolyzing agent; and removing the solvent; said components (a) and (b) each having a molecular weight of at least $10^4$.

2. The method of claim 1, wherein water is the protolyzing agent.

3. The method of claim 1 or 2, wherein the solvent is removed by evaporation at 100° to 200° C. in a closed system, in the presence of sufficient humidity to prevent dehydration of the protolyzed anhydride groups.

4. The method of claim 3, wherein the solvent is removed at a temperature of 130° to 160° C. and a pressure of 10 to 500 mm of Hg.

5. The method of claim 1, wheein component (a) is one or more copolymers of high molecular weight of an alkene-unsaturated monomer and maleic anhydride.

6. The method of claim 5, wherein component (a) is a styrene-maleic anhydride copolymer.

7. The method of claim 5, wherein an additional component or material is added during the preparation.

8. The method of claim 7, wherein the additional component is a foaming agent.

9. A homogeneous polymer alloy, stable up to high temperatures, prepared from a component (a) which is one or more polymers of high molecular weight having anhydride groups and a component (b) which is a cellulose ester; the component (a) being protolyzed, in whole or in part, and components (a) and (b) being linked to each other by hydrogen bonds.

10. The polymer alloy of claim 9, wherein component (a) is one or more copolymers of high molecular weight of an alkene-unsaturated monomer and maleic anhydride.

11. The polymer alloy of claim 10, wherein component (a) is a styrene-maleic anhydride copolymer.

12. The polymer alloy of claim 9 or 10, wherein an additional component or material is present.

13. The polymer alloy of claim 12, wherein the additional component is a foaming agent.

14. Formed products, such as granules, fibers, foils and foam, obtained from the polymer alloy of claim 9, 10 or 11.

15. The method of claim 7, wherein the additional component is a filler.

16. The polymer alloy of claim 12, wherein the additional component is a filler.

* * * * *